United States Patent
Zuhars et al.

(10) Patent No.: US 11,229,487 B2
(45) Date of Patent: *Jan. 25, 2022

(54) OPTICAL COMMUNICATION SYSTEM

(71) Applicants: Joel Zuhars, Fremont, CA (US); Saleh Tabandeh, Fremont, CA (US)

(72) Inventors: Joel Zuhars, Fremont, CA (US); Saleh Tabandeh, Fremont, CA (US)

(73) Assignee: Think Surgical Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/695,990

(22) Filed: Nov. 26, 2019

(65) Prior Publication Data

US 2020/0100848 A1 Apr. 2, 2020

Related U.S. Application Data

(63) Continuation of application No. 15/505,167, filed as application No. PCT/US2015/062107 on Nov. 23, 2015, now Pat. No. 10,507,063.

(Continued)

(51) Int. Cl.
| | |
|---|---|
| *H04B 10/116* | (2013.01) |
| *A61B 34/20* | (2016.01) |
| *A61B 90/00* | (2016.01) |
| *A61B 17/00* | (2006.01) |
| *A61B 90/30* | (2016.01) |
| *H04B 10/112* | (2013.01) |

(52) U.S. Cl.
CPC ............. *A61B 34/20* (2016.02); *A61B 90/39* (2016.02); *H04B 10/116* (2013.01); *A61B 90/30* (2016.02); *A61B 2017/00221* (2013.01); *A61B 2034/2055* (2016.02); *A61B 2090/397* (2016.02); *A61B 2090/3937* (2016.02); *A61B 2090/3945* (2016.02); *A61B 2090/3983* (2016.02); *H04B 10/112* (2013.01)

(58) Field of Classification Search
CPC .................... A61B 34/20; A61B 90/39; A61B 2017/00221; A61B 90/30; A61B 2090/3945; A61B 2090/3983; A61B 2090/3937; A61B 2090/397; A61B 2034/2065; H04B 10/116
USPC .................................. 398/118–131, 140–172
See application file for complete search history.

(56) References Cited

U.S. PATENT DOCUMENTS

| | | | |
|---|---|---|---|
| 6,892,090 B2 * | 5/2005 | Verard ................... | A61B 34/20 600/424 |
| 2002/0131121 A1 * | 9/2002 | Jeganathan ........ | H04B 10/1127 398/128 |

(Continued)

*Primary Examiner* — Dibson J Sanchez
(74) *Attorney, Agent, or Firm* — Blue Filament Law PLLC

(57) ABSTRACT

An optical tracking system includes at least one tracking array for generating and optically transmitting data between 1 and 2,000 MB/s. At least one tracker for optically receiving the optically transmitted data between 1 and 2,000 MB/s is also provided. The tracking system is used not only for tracking objects and sending tracking information quickly but also providing the user or other components in an operating room with additional data relevant to an external device such as a computer assisted device. Orthopedic surgical procedures such as total knee arthroplasty (TKA) are performed more efficiently and with better result with the optical tracking system.

20 Claims, 7 Drawing Sheets

Related U.S. Application Data

(60) Provisional application No. 62/083,052, filed on Nov. 21, 2014.

(56) References Cited

U.S. PATENT DOCUMENTS

| | | | | |
|---|---|---|---|---|
| 2003/0043435 A1* | 3/2003 | Oettinger | ........... | H04B 10/1149 398/129 |
| 2006/0142657 A1* | 6/2006 | Quaid | ................ | A61B 17/1764 600/424 |
| 2007/0239153 A1* | 10/2007 | Hodorek | ................ | A61B 34/20 606/41 |
| 2008/0009697 A1* | 1/2008 | Haider | ................... | A61B 90/11 600/407 |
| 2008/0119727 A1* | 5/2008 | Barbagli | ............... | A61B 8/0833 600/424 |
| 2008/0147089 A1* | 6/2008 | Loh | ................... | A61B 1/00149 606/130 |
| 2008/0218770 A1* | 9/2008 | Moll | ..................... | A61B 34/71 356/614 |
| 2010/0168562 A1* | 7/2010 | Zhao | ..................... | A61B 90/94 600/426 |
| 2010/0272442 A1* | 10/2010 | Lechner | ................. | A61B 34/74 398/106 |
| 2012/0308239 A1* | 12/2012 | Sheth | ................. | H04B 10/1125 398/131 |
| 2013/0236183 A1* | 9/2013 | Chao | ................... | H04B 10/116 398/101 |
| 2014/0088410 A1* | 3/2014 | Wu | ........................ | A61B 34/20 600/424 |
| 2014/0161466 A1* | 6/2014 | Riza | ................... | H04B 10/1143 398/119 |
| 2014/0248058 A1* | 9/2014 | Simpson | ............... | H04B 10/112 398/104 |
| 2015/0215040 A1* | 7/2015 | Dickson | ............. | H04B 10/1125 398/131 |
| 2016/0081753 A1* | 3/2016 | Kostrzewski | .......... | A61B 46/10 606/130 |
| 2016/0314710 A1* | 10/2016 | Jarc | ..................... | G09B 23/285 |
| 2017/0105713 A1* | 4/2017 | Frimer | ................ | A61B 1/0016 |

* cited by examiner

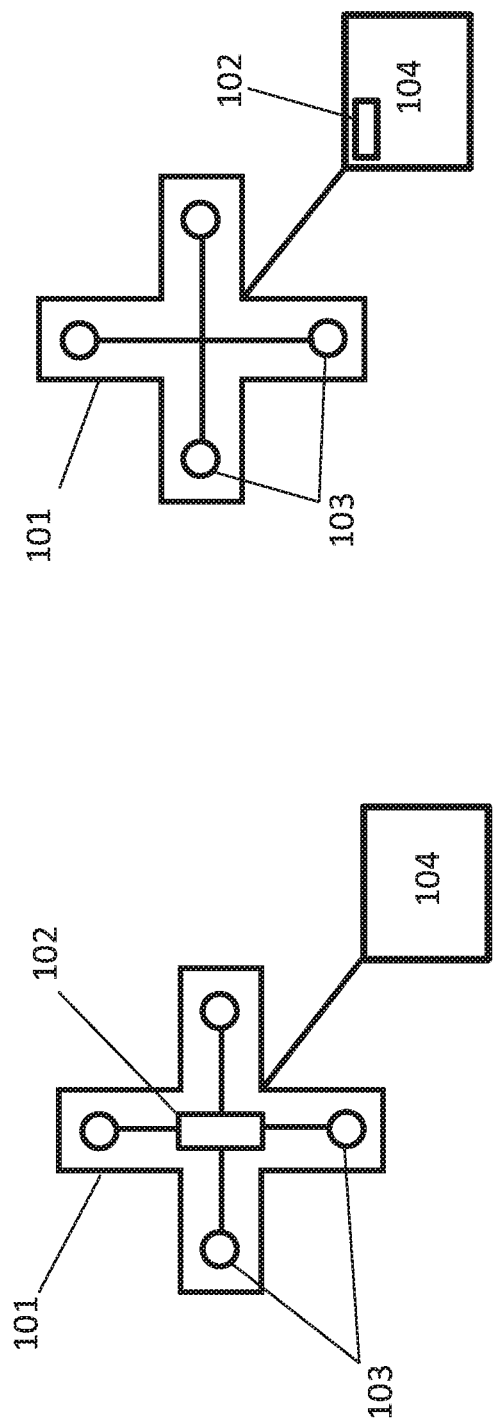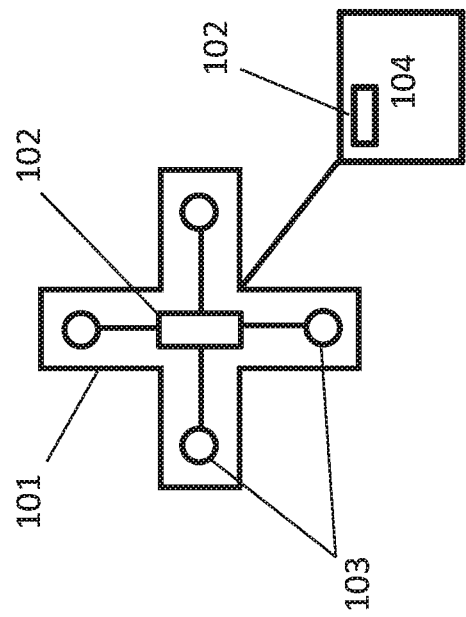

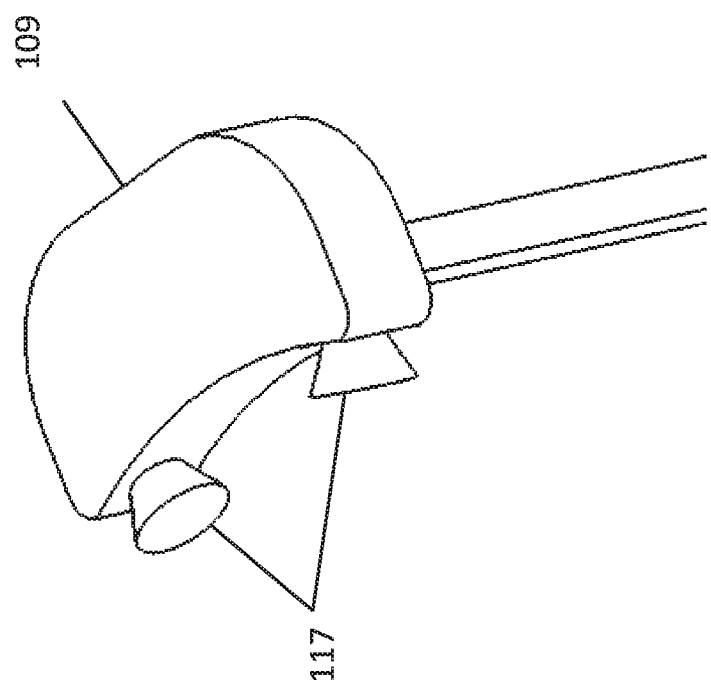

OPTICAL COMMUNICATION SYSTEM

RELATED APPLICATIONS

This application is a continuation application of U.S. patent application Ser. No. 15/505,167, filed Feb. 20, 2017, which is a 371 continuation of International Patent Application No. PCT/US2015/062107, filed on Nov. 23, 2015, which, in turn, claims the benefit of U.S. Provisional Application No. 62/083,052, filed on Nov. 21, 2014, the contents of which are hereby incorporated by reference.

TECHNICAL FIELD

The present disclosure generally relates to visible light communication systems, and in particular to data transmission between tracking systems and tracking markers in a surgical setting.

BACKGROUND

Tracking and navigation systems have been employed in various applications to accurately locate, track and navigate objects in space. In the medical field, tracking systems have been utilized with medical devices to assist surgeons in performing precision surgery.

Typical configurations and methods for tracking objects in an operating room are well known in the art. One such method exploits optical signals (light, radiofrequency, infrared, sound etc.) and optical receivers (photodiodes, CMOS or CCD cameras) to locate the position and orientation of medical devices relative to a patient's anatomy. Optical tracking systems are commonly used due to their accuracy and adaptability.

The optical tracking systems generally comprise the following. Three or more active or passive markers that emit or reflect optical signals are arranged in a known geometry on a tracking array. Two or more optical receivers are housed away from the patient in the operating room to receive signals emitted or reflected from the markers. A processing unit electrically connected to the optical receivers analyzes the incoming signals to calculate the position and orientation of the tracking array.

The tracking arrays are fixed to both a patient's anatomy and to the medical device. Using techniques well known in the art, the coordinate frames of the optical sensors, the tracking arrays, the patient's anatomy, and medical device can be calculated relative to each other. During surgery, the markers periodically emit or reflect signals that are captured by the optical sensors and processed to calculate the position and orientation of the medical device relative to the patient's anatomy of interest.

The tracking system described has been exploited for various medical applications. For example, the marker arrays have been attached to hand-held devices such as the ES2 Spinal System manufactured by Stryker. The surgeon can visualize pedicle screw placement relative to a patients vertebrae on a display monitor in the OR. Another application is to use the tracking system with a semi-active computer assisted device such as the RIO Robotic Arm Interactive Orthopedic System manufactured by Mako that provides visual feedback as to the position and orientation of a reamer during acetabular preparation in total hip arthroplasty. Similarly, the tracking system can be used with fully active computer assisted devices to provide location information that is sent to a control unit that guides movement of the device relative to a patient's anatomy.

Currently, the emitted or reflected signals from the markers merely provide a means to accurately detect the markers location in space and discern the marker from the background (signal to noise). However, there have been recent advancements in light emitting diode (LED) technology that provide a means to transmit data at higher rates than previously feasible that can serve a plurality of valuable uses especially in a medical setting.

Recently, data rates over 1.6 Gbit/s have been demonstrated using visible light emitted from LEDs and optical sensors like CCD or CMOS cameras. With the small size of the components needed, and ability to send signals long distances through electrical connections, several new applications arise every day for this technology. For example, LEDs can now be placed in various locations of a home, shopping center, department store or office work place to transmit data to computers, cell phones, fax machines, etc. The streamed data could connect users to the internet, send advertisements, provide location information etc.

Additionally, there are many advantages to using visible light to transmit data in contrast to traditional radio frequency. Radio waves can cause electromagnetic interference with surrounding electronic equipment and can penetrate walls, which is a potential security risk. Light, however, is confined to line of sight, poses no risk of electromagnetic interference and has approximately 10,000 times more bandwidth available compared to radio waves.

Considering traditional optical tracking systems already include LED markers and optical sensors, the systems can be altered to transmit tracking and additional information at theoretical rates in excess of 500 Mb/second to serve a plurality of functions. Unfortunately, the complexities of the surgical setting and high tolerances associated with surgery have prevented LED data transmission in the surgical setting.

Thus, there exists a need for a light based data transmission system. There further exists a need for such a system in the context of robotic surgery.

SUMMARY OF THE INVENTION

An optical tracking system includes at least one tracking array for generating and optically transmitting data between 1 and 2,000 MB/s. At least one tracker for optically receiving the optically transmitted data between 1 and 2,000 MB/s is also provided. The tracking system is used not only for tracking objects and sending tracking information quickly but also providing the user or other components in an operating room with additional data relevant to an external device such as a computer assisted device. Orthopedic surgical procedures such as total knee arthroplasty (TKA) are performed more efficiently and with better result with the optical tracking system.

BRIEF DESCRIPTION OF THE DRAWINGS

FIGS. 1A, 1B and 1C depict an inventive tracking array and external device with various configurations of a processing unit associated therewith.

FIG. 7 depicts a physical barrier place around a photosensor for data targeting.

DESCRIPTION OF THE PREFERRED EMBODIMENTS

Figure 2:
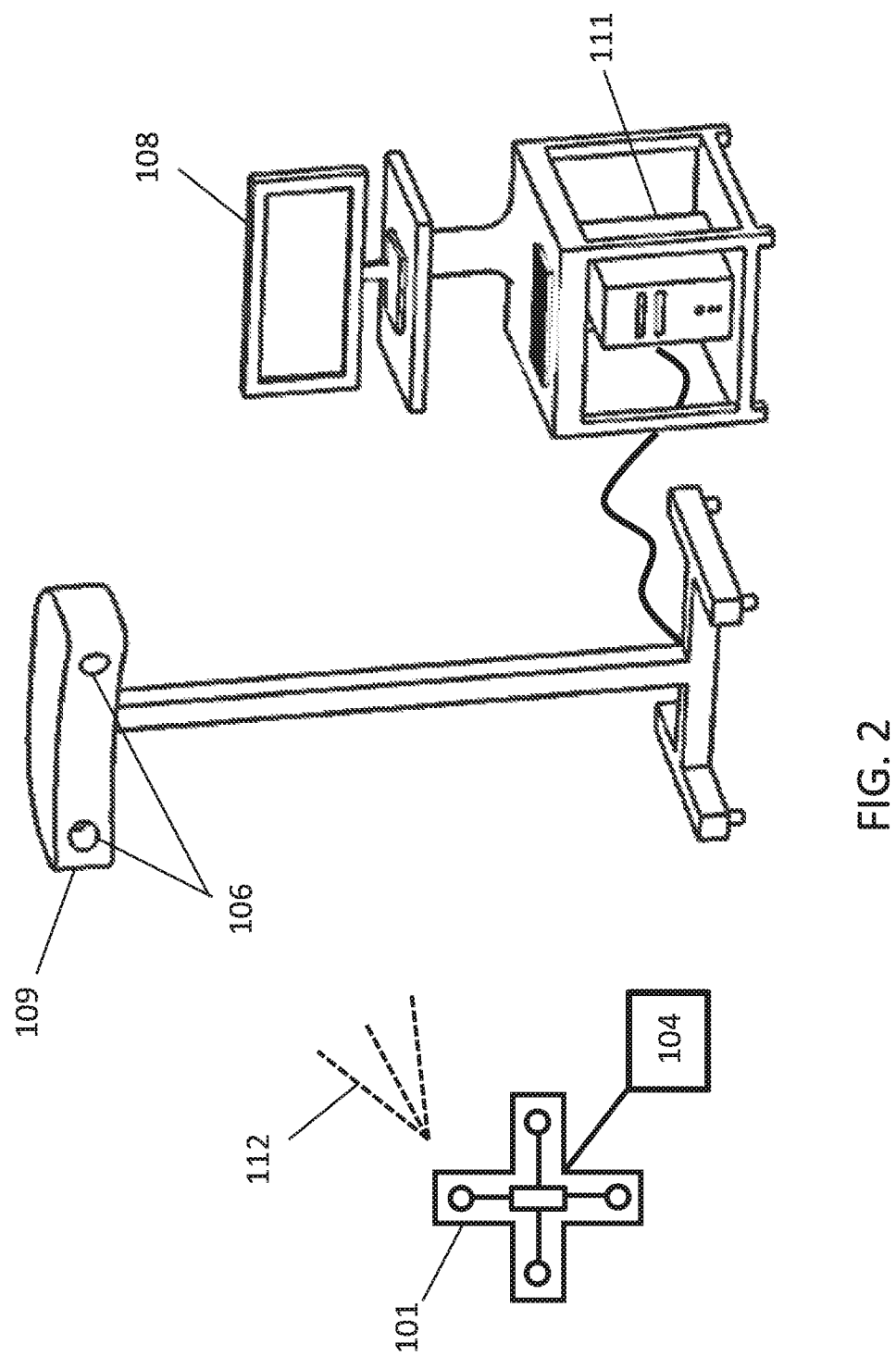
FIG. 2 shows an example of an inventive tracking system with elements disclosed herein.

The invention disclosed herein generally has utility as a method and device for using existing components of a tracking system to transmit data at high rates and more specifically to transmitting data between the tracking system, LED markers, and other external devices to be utilized in a medical setting, or patients within a medical setting.

It is to be understood that in instances where a range of values are provided that the range is intended to encompass not only the end point values of the range but also intermediate values of the range as explicitly being included within the range and varying by the last significant figure of the range. By way of example, a recited range from 1 to 4 is intended to include 1-2, 1-3, 2-4, 3-4, and 1-4.

As used herein, "high rate" is defined with respect to data transmission as encompassing rates of greater than 1 Mb/second; however, it is known in the art that LED actuation can currently encompass rates in the range of 1-2,000 Mb/second.

A major benefit of using the invention disclosed herein is the ability of the tracking system to be used not only for tracking objects and sending tracking information quickly but also providing the user or other components in the operating room with additional data relevant to an external device such as a computer assisted device. Such computer assisted devices illustratively include a robot, surgical saw, surgical drill, haptically controlled devices, autonomous and semi-autonomous surgical devices, and combinations thereof.

By way of example, total knee arthroplasty (TKA) requires the distal femur and proximal tibia to be cut to prepare the knee for a prosthetic knee implant. The position, slope and orientation of the cuts are critical to ensure the prosthetic is fitted correctly to restore the alignment of the knee joint. A TKA procedure generally involves the following. A surgeon will review a patient's MRI or CT scan, and assess the extent of the disease and preoperatively plan the procedure. Intraoperatively, the surgeon exposes the knee joint and uses a surgical saw typically with the assistance of patient specific jigs to accurately make the femoral and tibial cuts. After the cuts are made, trial implants are used to assess the patient's range of motion and fit of the implant. If the range of motion and fit are acceptable by the surgeon, the prosthesis is implanted and the knee is closed.

The markers described herein generally refer to any passive or active transmitter capable of reflecting or emitting signals such as visible light, radiofrequency, infrared, sound, and electromagnetic signals. More specifically, the invention discloses the use of active LED markers for tracking and/or transmitting data, and in particular, the LED markers for transmitting data may emit any spectrum/frequency of light but preferably in the wavelength range of 320 nanometers to 760 nanometers. As used herein, a tracking array is considered a configuration of a plurality of markers.

As used herein, a light emitting diode (LED) is defined as any light source capable of electrically modulated electroluminescence.

An LED operative in the present invention is readily made of a plurality of semiconductor materials known in the art to produce light at any spectrum/frequency. Examples of such materials illustratively include gallium arsenide phosphide, aluminum gallium indium phosphide, gallium(III) phosphide, zinc selenide, silicon, silicon carbide, indium gallium nitride, a nanocrystal- or dye-sensitized versions of any of the aforementioned, and any combinations thereof. It is also appreciated that an LED is readily procured commercially that is able to produce any wavelength is also defined herein. For example, it is known that the combination of red, green and blue LEDs emit white light or a single white light LED is also known to the art, as evidenced by H. S. Chen, C. K. Hsu, and H. Y. Hong, "InGaN—CdSe—ZnSe quantum dots white LEDs," IEEE Photon. Technol. Lett. 18(1), 193-195 (2006).

The types of tracking systems or trackers used in the medical field are well known in the art such as those described in U.S. Pat. No. 6,061,644. The accuracy and reliability of optical tracking systems has been a particular design challenge and is a function of many variables such as marker configuration, types of photosensors, signal processing methods, and the distance between the marker and the photosensors. A description of each variable is beyond the scope of the disclosed invention but it should be appreciated that the embodiments described herein may be adapted to any tracking system configuration.

Tracking Array and External Device Data Transmission

Now referring to FIG. 1A, the inventive optical tracking system includes a tracking array 101 having at least one LED 103 for data transmission and having at least one processing unit 102 that actuates the LED(s) 103 using a time or frequency domain modulation techniques to transmit data at high rates. The data to be transmitted is created by the internal processing unit 102 of the tracking array 101. In at least one embodiment of the present invention, the data to be transmitted is received by the tracking array 101 from an external device 104 using an electrical connection between the tracking array 101 and the external device 104 where the internal processor 102 can actuate the LEDs to send the data in as-developed, pre-processed, or processed form that is received from the external device. The processing unit 102 is capable of performing various signal processing operations for example but not limited to error-correction code encoding, modulation, interleaving, FFT/IFFT etc. The processor also includes at least one light-emitting element drive circuit to actuate the LEDs with the desired signal. In addition, the processing unit 102 is capable of modulating signals using techniques for example but not limited to on-off keying modulation, amplitude modulation, pulse width modulation, M-level quadrature amplitude modulation etc. The processing unit 102 capable of multiplexing signals using techniques for example, but not limited to, frequency division multiplexing, time division multiplexing, orthogonal frequency division multiplexing, and combinations thereof. In certain inventive embodiments, the processing unit 102 is further capable of multiplexing and modulating signals.

By way of example, an external device such as a 2-degree of freedom (2DOF) hand held drill as described in International App. No. PCT/US2015/051713 assigned to the assignee of the present application and incorporated by reference herein in its entirety, is equipped with the tracking array of the present invention by being mounted and electrically connected to the drill. In one inventive embodiment, the internal processor of the tracking array can send internal processor generated data through the LED(s) 103 (e.g. the data is an identification code of the tracking array or the data is inherent of the tracking array itself, or IMU data on the tracking array). While in another inventive embodiment, data from the 2DOF drill is sent to the internal processor which actuates the LEDs to wirelessly transmit data inherent of the drill (e.g. data about the cutting velocity of the drill tip, user prompts, forces experienced by the drill, and other data as described below).

In a particular embodiment of the present invention, the tracking array includes at least one LED 103 for high rate data transmission, and two or more active and/or passive markers that may emit or reflect optical signals such as visible light, radiofrequency, infrared, sound, or electromagnetic signals. The two or more active and/or passive markers may be specifically used for traditional tracking, while the actuated LED 103 is used specifically for data transmission. In a specific embodiment of the present invention, the tracking array includes two or more LEDs 103 capable of transmitting data at a high rate as shown in FIGS. 1A-C. It should be appreciated that the LED(s) 103 capable of transmitting data may also be used as the source for an optical tracker to track the tracking array and any object attached thereto, such as an external device 104.

In a particular embodiment of the present invention, the internal processing unit 102 is housed or located in/on an external device 104 and electrically connected to the individual LEDs 103 to control actuation as illustrated in FIG. 1B. The external device 104 may also house at least one processor for signal processing and is connected to an internal processor 102 of the tracking array 101 by an electrical connection as illustrated in FIG. 1C. The processor 102 housed in/on the external device 104 may also control the external device 104.

Tracker Data Receiver

Now referring to FIG. 2, the data 112 transmitted from the LEDs 103 is received by at least one photosensor 106 of a tracker 109. The tracker 109 is also capable of determining the position and orientation of a tracking array 101 and any object attached thereto using these photosensors 106 and any standard tracking, calibration and registration methods known in the art. It should be appreciated that the at least one photosensor 106 can be any detecting sensor known in the art, such as, but not limited to, a photodiode, CCD and/or CMOS camera. In at least one embodiment of the device, two or more photosensors 106 are arranged in a known configuration within the tracker 109. In a particular embodiment, there are two or more photosensors 106 dedicated to tracking and one or more additional photosensors dedicated to receiving the transmitted data 112. In at least one embodiment the tracker 109 is attached to a rigid structure with a base that can be placed in the operating suite as shown in FIG. 2.

In at least one embodiment of the present invention, the rigid structure with the tracker 109 attached includes components (not shown) to adjust the tracker 109 with the arranged photosensors 106 in at least one degree of freedom of a physical coordinate system. Coordinate systems for degree of freedom movement illustratively include Cartesian and spherical. In at least one embodiment of the present invention, the components are manipulated to adjust the tracker 109 with the arranged photosensor 106 manually by a user. In at least one embodiment of the present invention, the components for adjusting the tracker 109 with the arranged photosensor 106 may be controlled by a tracker processing unit and/or computer 111, or other processing unit (not shown) capable of translating and/or rotating the tracker 109 based on data generated from the LEDs 103 on the tracking array 101, a computer 111, and/or other external devices. In at least one embodiment of the present invention, a plurality of trackers 109 are located about the room.

Figure 3B:
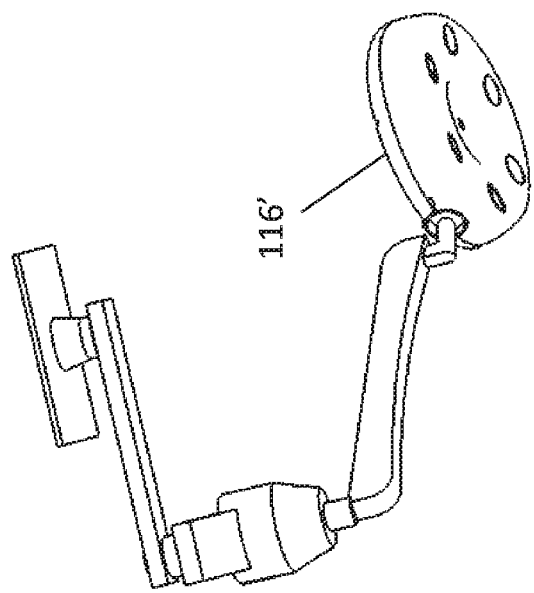
FIGS. 3A and 3B depict an inventive arrangement of photosensors attached to a surgical light in an operating room.
Figure 3A:
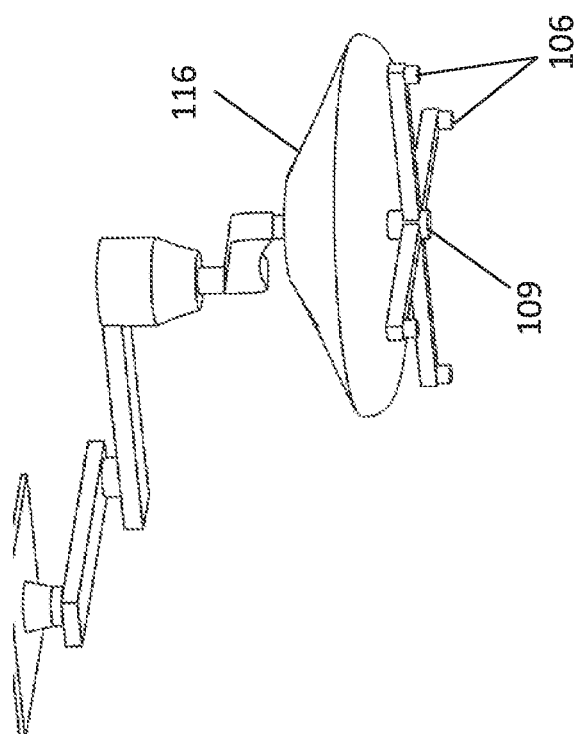

In at least one embodiment of the invention, the tracker 109 with photosensor 106 is attached to other objects in the room. Objects for tracker 109 attachments can be but not limited to the room walls, the room ceiling, the room floor, medical equipment, the surgical lights, and combinations thereof. In at least one embodiment, the tracker 109 may be configured to attach to specific objects in the room such as a surgical light 116 as shown in FIG. 3A or may be directly built into a surgical light 116' as shown in FIG. 3B.

The photosensor 106 are electrically connected to a tracker processing unit to inversely process the data 112 transmitted from the LED/s 103 and may also be the processor that determines the POSE of any tracked objects in the OR. The tracker processing unit is capable of recovering the received data using different signal processing techniques for example but not limited to demodulation, FFT/IFFT, error correction, deinterleaving, and a combination thereof. In at least one embodiment of the present invention, the photosensor 106 uses a digital or physical filter to single out specific LEDs and/or data frequencies. Illustratively, the types of physical filters may include but not limited to absorptive filters, dichroic filters, monochromatic, longpass, bandpass, shortpass, polarizers etc. Types of digital filtration may include but not limited to FFT/IFFT, bandpass, Kalman filters, Bessel filters, high-pass, low-pass, and combinations thereof.

The tracker processing unit may be located in/on the tracker 109 and/or is a part of the computer 111 and/or is located on the base of a rigid structure with the tracker 109 attached, and/or located on an external device.

Tracking Array and External Device Data Receiver

With reference to FIG. 4, the tracking array 101 includes at least one photosensor 113 to act as a data receiver. The photosensor 113 is any light detecting sensor illustratively including a photodiode, CCD and/or CMOS camera. The data received by the photosensor 113 in some embodiments of the present invention, is inversely processed and recovered with the internal processor 102, FIG. 4A, or alternatively, the data is transferred to a processor located on the external device using an electrical connection between the marker and the external device, FIG. 4B. In at least one embodiment of the present invention, the tracking array 101 includes an additional processing unit 114 electrically connected to the photosensor 113 devoted only to the inverse processing of the incoming data as shown in FIG. 4C.

Figure 4A:
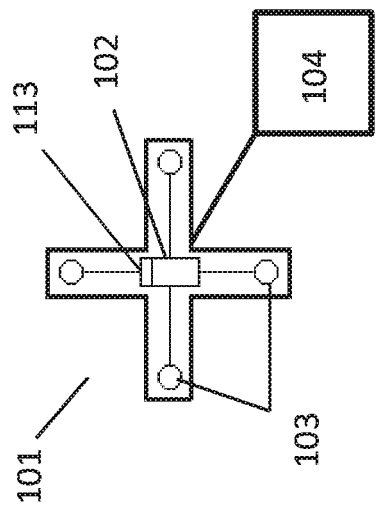
FIGS. 4A-4F depict various examples of an inventive tracking array and external device including processing units and/or photosensors attached therein.
Figure 4B:
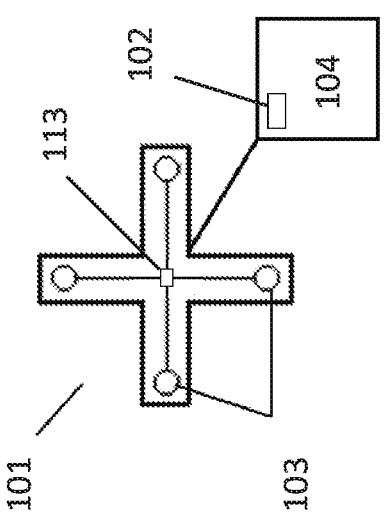
Figure 4C:
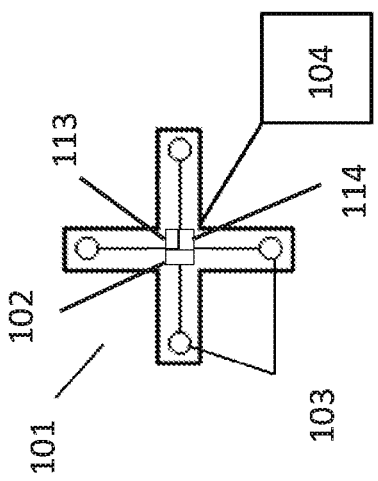
Figure 4D:
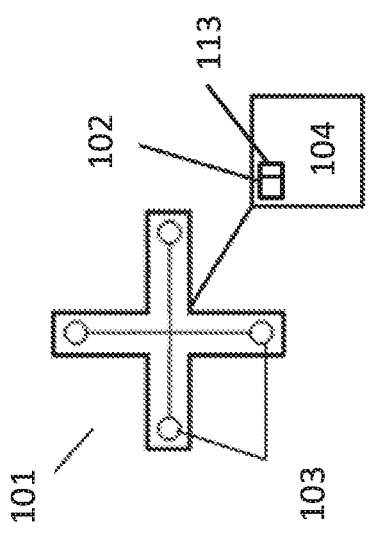
Figure 4E:
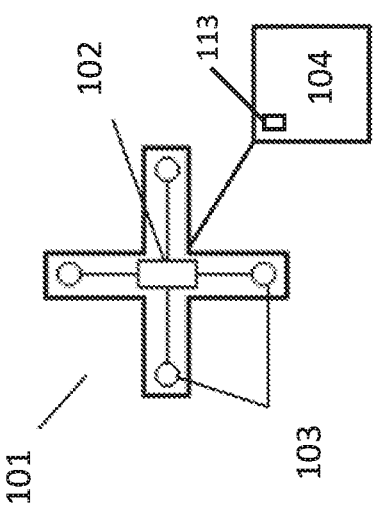
Figure 4F:
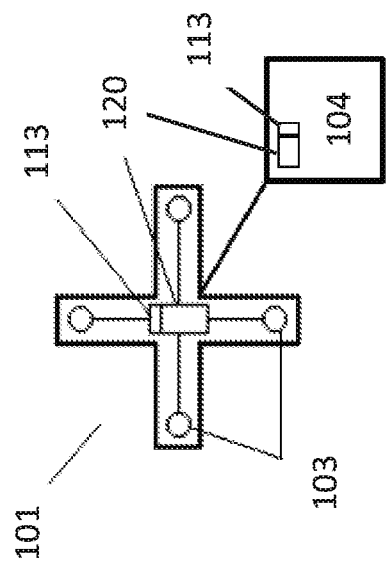

In at least one embodiment of the present invention, the photosensor 113 is located on the external device 104 to receive data that can be inversely processed and recovered using a processing unit on the external device, as shown in FIG. 4D. In at least one embodiment of the present invention, data received from the at least one photosensor 113 located on the external device 104 may be transferred by way of electrical connection to the internal processing unit 102 on the tracking array 101 to be inversely processed and recovered as shown in FIG. 4E. In at least one embodiment, both the tracking array and external device each have one photosensor and at least one processing unit that can receive and process data that can be transmitted between the tracking array and external device by way of electrical connection as illustrated in FIG. 4F.

In at least one embodiment, the processing unit 102 on the tracking array 101 and/or the external device 104 comprising components to inversely process the received signal by the photosensor 113. The processing unit 102 and/or 114 capable of recovering the received data using signal processing techniques such as but not limited to demodulation, FFT/IFFT, error correction, deinterleaving, etc. In at least one embodiment of the invention, the data is received by photosensor 113 on tracking array 101 and inversely processed by processing unit 102 and/or 114 where the processed data is then sent via an electrical connection to external device 104 to be utilized by the external device 104. In other embodiments, the data is received by photosensor 113 on the external device 104 and inversely processed by processing unit 102 and/or 114 where the processed data is then transferred at high rates with the LEDs 103 of the tracking array 101.

The embodiments depicted in FIGS. 4A-F show various configurations of photosensor/s and/or processing units 113, 114. The invention disclosed herein can include any combination of the examples show in FIGS. 4A-F and is intended for illustration and not meant to be limiting.

In at least one embodiment, the processing units 102 depicted in FIGS. 4A-F can actuate the LEDs to transmit data as well as process incoming data received by photosensor 113. The data to be transmitted can now be created by the processing unit 102 on the tracking array 101, from the external device 104, the processing unit of the external device 102, and/or from the data received by the at least one photosensor 113 and any combination thereof. It should be appreciated that the various combinations of data retrieval/transmittal, processing/inverse processing between the tracking array 101, external device 104, tracker 109, external device 110, computer 111, and any other device electrically connected and/or comprising a tracking array 101 may be utilized.

Tracker Data Transmission

Figure 5:
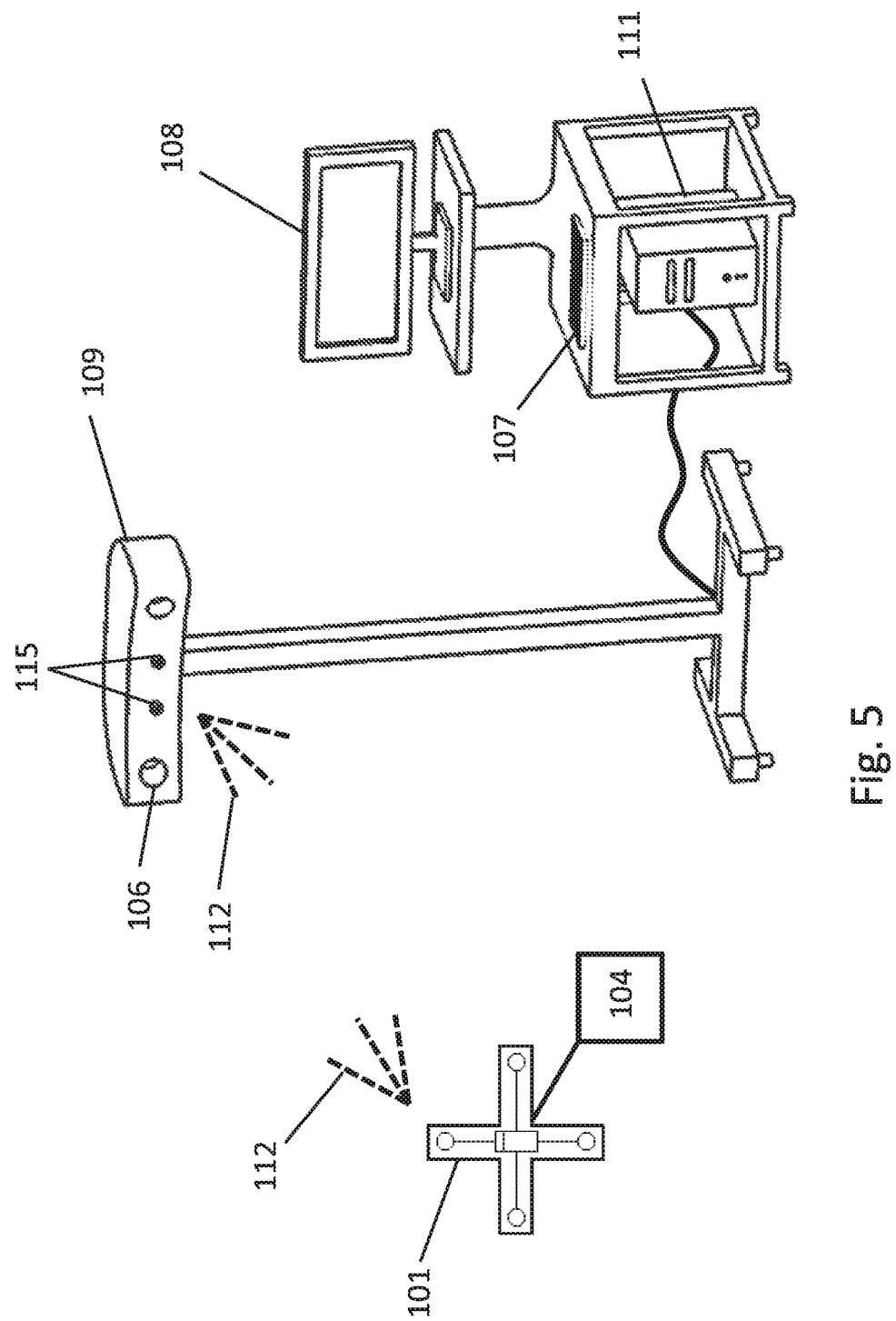
FIG. 5 is an inventive example of an arrangement of photosensors associated with light emitting diodes for data transfer.

With reference to FIG. 5, the tracker 109 may include at least one LED 115. The LED 115 is located on the tracker 109 and transmits data at high rates to a photosensor 113 located on the tracking array 101 and/or the external device 104. In at least one embodiment of the present invention, the LED 115 may be located near the photosensor/s 106 but not housed in a casing as described previously. For example, the LED 115 can be arranged on the same tracker 109 attached to a surgical light like the one depicted in FIG. 3A-B.

In at least one embodiment of the present invention, the LED 115 can be actuated to transmit data at high rates using components and methods as described for the processing unit 102 of the tracking array 101. In other embodiments of the present invention, the LEDs are actuated from the tracker processing unit, and/or from a computer 111, and/or from an external device and/or an additional processing unit (not shown) located in or externally electrically connected to the tracker 109.

The data to be transferred from the LED/s 115 on the tracker 109 can be created from a plurality of sources. By way of example and not meant to be limiting, the data can be created internally from the tracker processing unit, the processing unit can receive data from a user by way of a monitor 109, computer 111, keyboard 107 and mouse, the data can be created from a memory storage device (not shown) such as USB or from transferrable media such as CDs, the data could be created from an external device electrically connected to the tracker processing unit, and/or the data can be created from data sent by a tracking array 101 or external device 104.

Types and Functions of Data

The types of data transmitted/received by a plurality of devices, tracking arrays, or tracking systems can contain a plurality of different information to be used for a plurality of different functions. The types of data to be transmitted/received may contain the following information as an example and is no way meant to be limiting or necessary. For example, the data can contain identification and location of a specific LED, the operating status of an external device, the position and orientation of a patient's anatomy, prompts for controlling the external device, the hardware or software version of an external device, data logged by the external device, operating parameters of an external device, velocity profiles, position and orientation, acceleration, current, temperature, battery life, forces exerted by or on the device, warnings, interruptions, faults, the status of a pre-surgical plan, a surgical plan, medical image data for a surgical plan, the surgical plan application such as an executable program, and binary streams of data. One of ordinary skill in the art should appreciate the multi-dimensional possibilities of data types and information that can be transmitted with the present invention especially as it relates to computer assisted medical devices.

In at least one embodiment of the present invention, the transmitted data is used to track movement of the marker LED's. It should be appreciated that through the use of Doppler algorithms, that several types of movement may be measured such as 3 dimensional movement of equipment within a space, body movements, body orientation, respiratory rates, and the like. Three dimensional data generated by the present invention includes imagery illustratively including patient body structure, equipment, and combinations thereof; dynamic interactions therebetween; position of at least one marker in a coordinate space; dynamic positional changes between markers; and combinations of the aforementioned.

In at least one embodiment, the LED markers may be used to monitor sleep apnea. In at least one embodiment of the present invention, the motion of the marker LEDs is monitored in real-time. In other embodiments of the present invention, LED markers are used to synchronize a patient's movement in real-time to medical equipment. In at least one embodiment of the present invention, the LED markers are used to synchronize movement of a patient to the movement of one or more medical linear accelerators to maximize targeting of a tumor to be treated by adjusting the radiotherapy beam to the patients movement, thus maximizing radiation dose to the tumor site, while minimizing collateral damage to surrounding tissue and organs.

Similarly, the data transmitted/received by a plurality of devices, tracking arrays, tracking systems, and/or combinations thereof can be used for a plurality of different functions. For example, but in no way meant to be limiting or necessary, in at least one embodiment the data is displayed directly to a monitor 109 or relayed to other external devices, the data could prompt a user to perform a task, the data is a set of instructions for an external device to execute such as a surgical plan, the data can instruct external devices in the surgical field to move based on the position and/or orientation of another device with a tracking array 101 and/or external device 104, external devices may be instructed to move based on the position and orientation of a patient's anatomy that is being tracked.

Data Targeting

Figure 6:
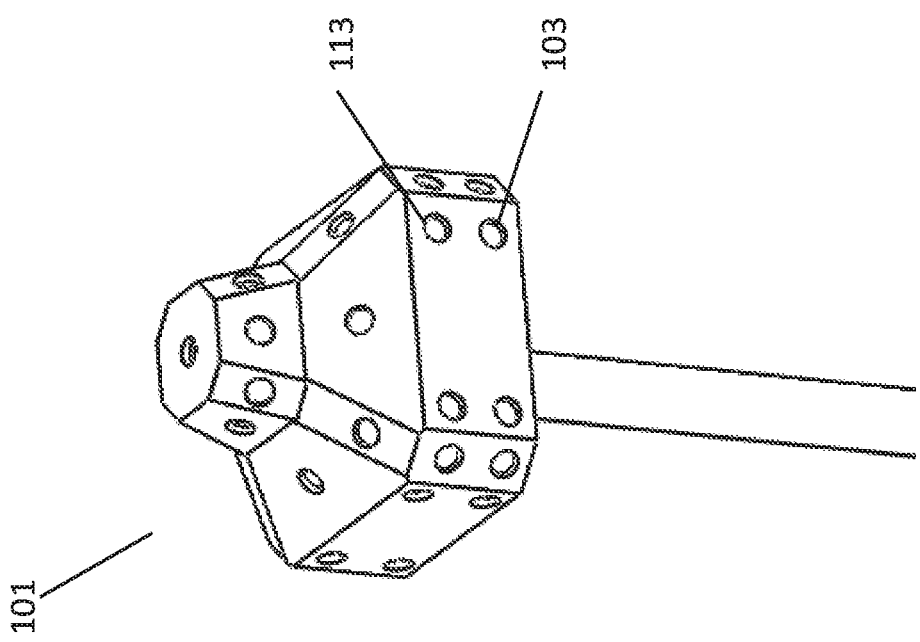
FIG. 6 depicts a multi-faced inventive tracking array comprising LEDs and/or photosensors that can be exploited for data link targeting.

In at least one embodiment of the invention, the data transmitted/received can be targeted to/from specific photosensors and LEDs. Targeting of specific tracking arrays, LEDs, and/or photosensors can be achieved by many different methods. In at least one embodiment, the field of view of the LED/s and or photosensor/s is limited to a specific range. For example, a typical emission field of an LED is 120 degrees conically. An LED and/or photosensor, or a combination thereof can be arranged in various configurations on a tracking array that contains multiple faces such as that shown in FIG. 6. The emission/receiving field of the LEDs/photosensors creates locations where the emitted/received signals are at a higher strength based on the orientation of the tracking array. Due to the ability to transfer data at high rates, a face that emits/receives signals at a higher strength can be targeted as an 'active' face. Data to be transmitted/received can therefore be directed to/from the 'active' face.

In at least one embodiment of the present invention, the targeting is achieved by limiting the data link to only the photosensor/s and LED/s that are in line of sight. A processing unit may compute the absence of a data link from an LED that has been obstructed from the line of sight of a photosensor. The data emitted/received from the obstructed LED/photosensor can cease and the data to be transmitted/received may be transferred/targeted to another LED and/or photosensor that is/are more 'active'. Therefore, data can be transferred to computing devices in the surgical suite, alone or in combination with also being used with at least one of targeted to/from specific LEDs, photosensors, tracking arrays, tracking array faces, external devices, and trackers.

In at least one embodiment of the present invention, the LEDs are actuated at the same time to create a redundant transmission system in which even if one marker is not seen by the photosensors, the data is still transmitted correctly. For example, the LED/s can be co-located with each photosensor to create a redundant multi-photosensor system. Therefore, if one or more of the photosensors are blocked along with their associated LED, the other LEDs can still be used to track and transmit data. In another example, multiple photosensors can be co-located on the tracker to create another redundant multi-photosensor system. If one photosensor is blocked, another photosensor located on the tracker may still be visible to receive data by a transmitting LED.

Additionally, the LEDs can be actuated independently to increase the data transmission rate. In at least one embodiment, individual LEDs can transmit different types of data independent of the other LEDs. By way of example, one LED continually sends the operating status of the external device 104, while an adjacent LED continually sends velocity data of the external device 104. In at least one embodiment of the present invention, the LEDs are actuated sequentially to transmit specific data to improve the chance the data is received in the event one or more LEDs become obstructed from the photosensors 106. For example, a first LED transmits the operating status of the external device for a given period of time, then the operating status of the external device is transmitted by a second LED for another period of time, then the data is transmitted by a third LED, and continues to be transmitted by additional LED's as may be needed. Therefore, in circumstances where the first and second LED are obstructed from the line of sight of the photosensors 106, eventually the third LED, or some other LED, will transmit the operating status of the external device.

In at least one embodiment, there are two or more modes or settings of data transfer rates. Illustratively, one mode can send data at a rate of around 1 Mb/s, while another mode can send data at a rate around 10 Mb/s. The mode at 1 Mb/s can illustratively send data such as the identity of the tracking array or LED and other 'background' information, and the other mode at 10 Mb/s can send tracking information. The mode at 10 Mb/s can also illustratively be used to send data such as the surgical plan, application executable transfer for software upgrades and other data that may be in the form of larger packets. In one embodiment, the change from one mode to another can be automatically made by the size of the data to be transferred. Illustratively, a computer knows the size of the data to be delivered and communicates to the processor 107 to switch to the 10 Mb/s data transfer mode if the data is large. The processor 107 can send an initial signal by actuating LEDs 115 to the photosensor 113 of the tracking array and processor 102 to switch to the receiving mode that can then collect and read the data at the appropriate data rate.

In another embodiment, the data is sent in two or more modes in parallel. By way of illustration, the tracking array sends identity information at one mode of 1 Mb/s while additionally sending tracking information at the other mode of 10 Mb/s. As 1 Mb/s and 10 Mb/s are given here as an example, it should be appreciated by one skilled in the art that higher or lower data rates can be accomplished with the present invention.

Multichannel transmission may also be accomplished by having a different wavelength or having a different type of modulation for each of the transmitting LEDs. One LED may transmit data at a first wavelength and another LED, either on the same tracking array or a separate tracking array, may transmit day at a second wavelength. This creates a multichannel transmission system that can be used to distinguish separate tracking arrays/external devices, or to send different types of data.

In a particular embodiment, the data may be targeted using a physical barrier placed around the photosensors. With reference to FIG. 7, a tracker 109 is shown with a conical physical barrier 117 placed around the photosensors of the tracker 109. The physical barrier 117 may have a conical angle less than emission field of the transmitting LED(s). If the tracker 109 is adjustable via mechanisms described above, than the photosensors of the tracker may be direct to specific tracking arrays or transmitting LEDs in the OR. Therefore, only the data from those LEDs are transmitted to the tracker 109. The physical barriers may of any shape or size and located around any of the photosensors on the tracker, the tracking arrays, or external device(s).

It should be appreciated that the invention disclosed herein can create a high-speed data network between a plurality of devices, a patient's anatomy, tracking arrays and multiple tracking systems in the operating room. Additionally, the data can be targeted to/from specific transmitters/receivers that can be useful in many applications and distinguishes itself from the typical light fidelity (LiFi) concept Additional Tracking Units In at least one embodiment of the present invention, additional tracking components known in the art can be attached to the tracking array 101 to provide additional information as to position and orientation. By way of example, inertial measurement units (IMUs) which include gyroscopes and accelerometers to calculate rotational and translational movement given a starting reference location may be used. The data from the IMU could be processed by the internal processor 102 of the tracking array and transmitted with the LEDs 103 to the photosensor 106 of the tracking system and subsequently to other external devices. The data from the IMU and the detected position of the LEDs on the tracking array could be fused and processed by the processing unit 107 that could improve the latency periods seen with current optical tracking systems. Additionally, with current tracking systems, when only one LED 103 is in line of sight of the photosensor 106, the position and orientation of the other LEDs are estimated based on their previous location and velocity vectors calculated by the processor 107. By using the additional position and orientation information from the IMU and having the ability to still transfer the data at a high rate from that LED, the accuracy of the estimated position and orientation is increased. Thus, by employing the IMU, traditional tracking system and the ability to transfer data at high rates, both the latency period and accuracy for tracking, navigating and guiding a computer assisted medical device is greatly improved.

It should be appreciated that IMUs have an internal problem of accumulating errors as the initial reference location starts to drift. Drift can cause errors with the true location and orientation of the tracker array in space. In at least one embodiment, to overcome IMU drift, an additional GPS unit is connected to the IMU to provide a global reference location. In at least one embodiment, the tracking system can re-set the reference location of the IMU when the LEDs are visible by a photosensor and would not require a GPS unit.

EXAMPLE

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

An optical tracking system is used with the patient's anatomy and a haptically guided hand-held surgical saw to assist a user in performing total knee arthroplasty. One tracking array 101 is electrically connected to the surgical saw 104, while additional tracking arrays 101 are fixed to the patient's femur and tibia near the surgical site. The user places the haptically guided surgical saw in a general area around the exposed femur and tibia. The surgeon by way of a monitor confirms a pre-operative or intra-operative surgical plan in the operating room. The surgical plan data is modulated and/or multiplexed by the processor 107, which then actuates the LEDs 115 on the tracker 109 accordingly to send the data at a high rate. The data is received by the photosensors 113 or 114 and read by the tracking processor 102 of the tracking array 101 on the surgical saw. The surgical plan data is read and causes the activation of haptic feedback mechanisms in the surgical saw to adjust the user's orientation and position in the correct place to make a femoral or tibial cut according to the plan.

Data between the tracking arrays on the patient and the tracking array on the surgical saw can also aid in correctly placing the surgical saw. If the orientation of the tracking array is known relative to the patient anatomy, and the orientation of the tracking array is known on the surgical saw, then the signal strength between different faces of the tracking arrays may aid in locating the correct plane. If certain faces are aligned between the tracking arrays, then the signal strength of data between the two can be used for positioning (LED data targeting. Additionally, as the haptic feedback mechanisms are assisting in adjusting the position and orientation of the saw, data about the operation of the feedback mechanisms can be relayed by the tracking array 101 on the saw back to the tracker and displayed on a monitor via the appropriate actuation of LEDs 103 by the internal processor 102. No electrical connections are required between the tracker unit and surgical saw.

As the surgical saw is cutting the defined plane, the tracking array 101 via the LEDs 103 sends operating data of the surgical saw including the operating velocity, the forces experienced at the saw tip, how much bone is being removed, the accuracy of the position and orientation of the planar cut, and warnings if the device is encountering soft tissue. The tracking array on the patient's anatomy receives data that the surgical saw is aligned, misaligned, or endangering specific structures and transmits data to the tracking system and the surgical saw to confirm the correct alignment, correct and or pause the surgical saw if it is misaligned, or send a warning to the user if there is a potential safety concern. After the surgical saw is completed with its task, the surgical saw transmits a prompt to the user asking for new instructions.

While at least one exemplary embodiment has been presented in this foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof. Additionally, as medical applications were presented herein, it should be understood that this technology could be implemented in other industries as well.

The invention claimed is:

1. A robotic surgical system, comprising:
a robotic surgical device having one or more processors and a photosensor in communication with at least one of said one or more processors;
a first set of at least three active light emitting diodes (LEDs), wherein at least one of said at least three active LEDs is a first data-transmitting-LED in communication with at least one of said one or more processors and transmitting data, wherein at least one of said one or more processors modulate the first data-transmitting-LED to transmit the data, the data inherent to the robotic surgical device, and wherein at least three active LEDs from said at least three active LEDs emit signals to permit tracking of a position and orientation of the robotic surgical device;
at least one tracker for line-of-sight tracking of the robotic surgical device and receiving said data inherent of the robotic surgical device; and
a second data-transmitting-LED on said at least one tracker, wherein the second data-transmitting-LED is modulated to transmit additional data used to execute or be executed by the robotic surgical device to implement a surgical plan, the additional data is associated with the surgical plan or is positional data as to the robotic surgical device to cause the robotic surgical device to adjust at least one of a position or orientation of a tool operated by the robotic surgical device.

2. The robotic surgical system of claim 1 wherein the additional data further comprises a position for a tool of the robotic surgical device to be placed relative to a position of a patient's anatomy.

3. The robotic surgical system of claim 2 wherein the patient's anatomy is a femur or tibia.

4. The robotic surgical system of claim 1 wherein the data includes at least one of an operating status, logged data, an operating parameter, battery life, a warning, or a fault.

5. The robotic surgical system of claim 1 wherein said at least three active LEDs are arranged on a tracking array coupled to the robotic surgical device.

6. The robotic surgical system of claim 5 wherein the tracking array contains at least one of said one or more processors of the robotic surgical device.

7. The robotic surgical system of claim 5 wherein at least one of said one or more processors are contained in the robotic surgical device and in communication with the first data-transmitting-LED on the tracking array.

8. The robotic surgical system of claim 1 wherein said at least three active LEDs are a configuration of at least three active LEDs on the robotic surgical device.

9. The robotic surgical system of claim 1 wherein said photosensor is a photodiode, charge coupled device, complementary metal-oxide-semiconductor camera, or combination thereof.

10. The robotic surgical system of claim 1 wherein said tracker further comprises a tracker processing unit and a computer with machine readable instructions to read the transmitted data and track the robotic surgical device.

11. The robotic surgical system of claim 1 wherein the robotic surgical device is a hand-held robotic surgical device.

12. A method for executing a surgical procedure with the surgical system of claim 1, the method comprising:

tracking a surgical device and a patient's anatomy with a tracker;

transmitting surgical planning data from an active LED on the tracker to a photosensor;

processing the surgical planning data with one or more processors;

adjusting at least one of a position or orientation of a bone cutting tool operated by the surgical device based on: a) the surgical planning data, b) the tracked position of the surgical device, and c) the tracked position of the patient's anatomy; and modifying the patient's anatomy with the bone cutting tool according to the surgical planning data.

13. The method of claim 12 further comprising transmitting data inherent of the surgical device to the tracker via a first data transmitting LED.

14. The method of claim 13 wherein the data inherent of the surgical device includes at least one of an operating status, logged data, an operating parameter, battery life, a warning, or a fault.

15. The method of claim 12 wherein the patient's anatomy is a femur or tibia.

16. The method of claim 15 wherein the surgical planning data includes a position or orientation for one or more cuts to be made on the femur or tibia.

17. The method of claim 12 wherein the surgical device automatically adjusts the tool according to: a) the surgical planning data, b) the tracked position of the surgical device, and c) the tracked position of the patient's anatomy.

18. The method of claim 12 wherein the surgical planning data transmitted from the active LED on the tracker includes at least one of operational, informational, positional, or instructional data used to execute or be executed by the surgical device to implement a surgical plan.

19. The method of claim 12 wherein the surgical planning data transmitted from the active LED on the tracker is a position for said bone cutting tool of the surgical device to be placed relative to a position of a patient's anatomy.

20. The robotic surgical system of claim 1 wherein said first data-transmitting-LED emits light conically.

* * * * *